(12) United States Patent
Wolff et al.

(10) Patent No.: US 7,524,680 B2
(45) Date of Patent: *Apr. 28, 2009

(54) POLYAMPHOLYTES FOR DELIVERING POLYIONS TO A CELL

(75) Inventors: Jon A. Wolff, Madison, WI (US); James E. Hagstrom, Middleton, WI (US); Vladimir G. Budker, Middleton, WI (US); Vladimir S. Trubetskoy, Madison, WI (US)

(73) Assignee: Roche Madison Inc., Madison, WI (US)

( * ) Notice: Subject to any disclaimer, the term of this patent is extended or adjusted under 35 U.S.C. 154(b) by 1652 days.

This patent is subject to a terminal disclaimer.

(21) Appl. No.: 10/095,681

(22) Filed: Mar. 11, 2002

(65) Prior Publication Data

US 2007/0071823 A1     Mar. 29, 2007

Related U.S. Application Data

(63) Continuation-in-part of application No. 09/753,990, filed on Jan. 2, 2001, now Pat. No. 6,383,811.

(51) Int. Cl.
*C12N 15/88*     (2006.01)
(52) U.S. Cl. ..................................... 435/458; 536/23.5
(58) Field of Classification Search ....................... None
See application file for complete search history.

(56) References Cited

U.S. PATENT DOCUMENTS 6,629,969 B2 * 10/2003 Chan et al. ................... 604/508
7,033,607 B2 * 4/2006 Trubetskoy et al. ......... 424/450

* cited by examiner

*Primary Examiner*—James S Ketter
(74) *Attorney, Agent, or Firm*—Kirk Ekena; Mark K. Johnson

(57) ABSTRACT

An polyampholyte is utilized in a condensed polynucleotide complex for purposes of nucleic acid delivery to a cell. The complex can be formed with an appropriate amount of positive and/or negative charge such that the resulting complex can be delivered to the extravascular space and may be further delivered to a cell.

14 Claims, 5 Drawing Sheets

SEQUENCE LISTING

<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Lys Asp Glu Leu
1

POLYAMPHOLYTES FOR DELIVERING POLYIONS TO A CELL

This Application is a Continuation-In-Part of Ser. No. 09/753,990, now U.S. Pat. No. 6,383,811, filed on Jan. 2, 2001.

FIELD OF THE INVENTION

The invention relates to compounds and methods for use in biologic systems. More particularly, polyions are utilized for modifying the charge ("recharging") of particles, such as molecules, polymers, nucleic acids and genes for delivery to cells.

BACKGROUND

Polymers are used for drug delivery for a variety of therapeutic purposes. Polymers have also been used in research for delivery of nucleic acids (polynucleotides and oligonucleotides) to cells, the process is one step in reaching a goal of providing therapeutic processes (gene therapy). One of the several methods of nucleic acid delivery to the cells is the use of DNA-polyion complexes. It has been shown that cationic proteins like histones and protamines or synthetic polymers like polylysine, polyarginine, polyornithine, DEAE dextran, polybrene, and polyethylenimine may be effective intracellular delivery agents while small polycations like spermine are ineffective.

In terms of intravenous injection, DNA must cross the endothelial barrier and reach the parenchymal cells of interest. The largest endothelia fenestrae (holes in the endothelial barrier) occur in the liver and have an average diameter from 75-150 nm. The trans-epithelial pores in other organs are much smaller, for example, muscle endothelium can be described as a structure which has a large number of small pores with a radius of 4 nm, and a very low number of large pores with a radius of 20-30 nm. The size of the DNA complexes is also important for the cellular uptake process. After binding to the target cells the DNA-polycation complex should be taken up by endocytosis.

Applicants have provided a process for delivering a compound across the endothelial barrier to the extravascular space and then to a cell.

SUMMARY

Described in a preferred embodiment is a process for enhancing delivery of a polyion to a cell, comprising the formation of a complex of polyampholyte and polyion. Then, delivering the complex into a cell.

In another preferred embodiment, we describe a process for extravasation of a complex. The process comprises the formation of a complex of polyampholyte and polyion. Then, inserting the complex into a vessel and delivering the complex to an extravascular space.

Reference is now made in detail to the preferred embodiments of the invention, examples of which are illustrated in the accompanying drawings.

DETAILED DESCRIPTION

Polyampholytes are copolyelectrolytes containing both polycations and polyanions in the same polymer. In aqueous solutions polyampholytes are known to precipitate near the isoelectric point and form micelle-like structures (globules) at the excess of either charge. Such globules maintain tendency to bind other charged macromolecules and particles (see R R Netz, J F Joanny, Macromolecules, 31, 5123-5141 (1998)).

In provisional application Ser. No. 60/093,153 we described gene transfer activity which can be substantially increased by adding polyanions to preformed DNA/polycation complexes(i.e. recharging). We confirmed the same phenomenon for cationic lipids (provisional application Ser. NO. 60/150,160).

Figure 1:
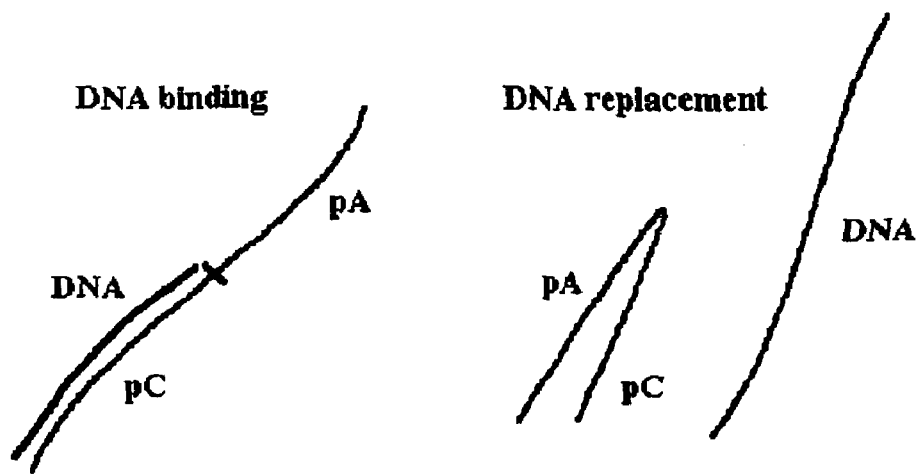
FIG. 1 DNA interactions with pC-pA block polyampholyte: binding (pA low charge density) and replacement (pA high charge density).

In this application we extend this principle into situations where DNA-binding polycation and polyanion are covalently linked into one polymer. Polyanions (polyanion=pA; polycation=pC) of higher charge density can displace DNA from its complex with polycation while pAs with lower charge density form triple complexes in which the complexes have a negative surface charge (Y Xu, F C Szoka, Jr., Biochemistry, 35, 5616-5623, (1996), V S Trubetskoy, A Loomis, J E Hagstrom, V G Budker, J A Wolff, Nucleic Acids Res. 27, 3090-3095 (1999)). Similarly, one can expect formation of DNA/polyampholyte complex in situations where a polyanion block ionically attached to a polyampholyte possesses a charge density lower than the charge density of the DNA molecule; A DNA molecule will be released from a complex with a polyampholyte when a polyanion block has a charge density higher than the DNA molecule (see FIG. 1). In the latter case, an internal pA-pC salt is formed.

It has previously been demonstrated that binding of negatively-charged serum components can significantly decrease gene transfer efficacy of DNA/polycation (DNA/pC) complexes in vivo (Vitiello L, Bockhold K, Joshi P B, Worton P B, Gene Therapy 5, 1306-13 (1998); Ross P C, Hui S W, Gene Therapy 6, 651-659 (1999). We have found that addition of polyanions to the point of near complex charge reversal drastically increases the efficacy of gene transfer mediated by DNA/pC complex upon i/v administration in mice (Provisional application Ser. No. 60/093,153). This improvement takes place due to protecting effect of pA which is situated as an outside shell on the triple complex and functions by inhibiting interactions of the complexes with serum proteins. We believe that gene transfer increase observed with DNA/polyampholyte complexes is based on the same phenomenon. The polyanion portion of polyampholyte being displaced from DNA/pC interaction can form an outside "shell" of negative charge and protect the complex from inhibiting interactions with serum proteins. The charge density of the pA is of primary importance. The higher charge density, the more effective is the protective effect against serum proteins.

In some cases a polyanionic block may be a natural protein or peptide used for cell targeting or other function. A polyanionic block can provide other functions too: for example, poly(propylacrylic acid) is known for pH-dependent membrane-disruptive function (Murthy N, Robichaud J R, Tirrell D A, Stayton P S, Hoffman A S, Controlled Release (1999) 61:137-43).

To demonstrate the principle we synthesized two block polyampholytes of linear polyethyleneimine (lPEI) with 1) polymethacrylic acid (lPEI-pMAA, high charge density pA) and polyglutamic acid (lPEI-pGlu, low charge density pA) and prepared complexes with plasmid DNA (pCIluc). We show that a covalent complex between pC and pA can substantially enhance gene transfer activity when compared to a non-polyampholyte mixture. We further describe the phenomena in the examples section of this application.

In this specification, the use of the term polyanion may refer to the anionic portion of the polyampholyte and the term polycation may refer to the cationic portion of the polyampholyte. Abbreviations: Poly-L-Lysine (PLL), succinic anhydride-PLL (SPLL), polymethacrylic acid, pMAA and polyaspartic acid, pAsp Polymers A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

To those skilled in the art of polymerization, there are several categories of polymerization processes that can be utilized in the described process. The polymerization can be chain or step. This classification description is more often used that the previous terminology of addition and condensation polymer.

Step Polymerization: In step polymerization, the polymerization occurs in a stepwise fashion. Polymer growth occurs by reaction between monomers, oligomers and polymers. No initiator is needed since there is the same reaction throughout and there is no termination step so that the end groups are still reactive. The polymerization rate decreases as the functional groups are consumed.

Typically, step polymerization is done either of two different ways. One way, the monomer has both reactive functional groups (A and B) in the same molecule so that A-B yields -(A-B)-

Or the other approach is to have two difunctional monomers.

A-A+B-B yields -(A-A-B-B)-

Generally, these reactions can involve acylation or alkylation. Acylation is defined as the introduction of an acyl group (—COR) onto a molecule. Alkylation is defined as the introduction of an alkyl group onto a molecule.

"If functional group A is an amine then B can be (but not restricted to) an isothiocyanate, isocyanate, acyl azide, N-hydroxysuccinimide, sulfonyl chloride,aldehyde (including formaldehyde and glutaraldehyde), ketone, epoxide, carbonate, imidoester, carboxylate activated with a carbodiimide, alkylphosphate, arylhalides (difluoro-dinitrobenzene), anhydride, or acid halide, p-nitrophenyl ester, o-nitrophenyl ester, pentachlorophenyl ester, pentafluorophenyl ester, carbonylimidazole, carbonyl pyridinium, or carbonyl dimethylaminopyridinium. In other terms when function A is an amine then function B can be acylating or alkylating agent or amination agent.

If functional group A is a sulfhydryl then function B can be (but not restricted to) an iodoacetyl derivative, maleimide, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then function B can be (but not restricted to) adiazoacetate or an amine in which a carbodiimide is used. Other additives may be utilized such as carbonyldiimidazole, dimethylamino pyridine (DMAP), N-hydroxysuccinimide or alcohol using carbodiimide and DMAP.

If functional group A is an hydroxyl then function B can be (but not restricted to) an epoxide, oxirane, or an amine in which carbonyldiimidazole or N,N'-disuccinimidyl carbonate, or N-hydroxysuccinimidyl chloroformate or other chloroformates are used. If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one bifunctional monomer so that A-A plus another agent yields -(A-A)-. If function A is a sulfhydryl group then it can be converted to disulfide bonds by oxidizing agents such as iodine (I2) or NaIO4 (sodium periodate), or oxygen (O2). Function A can also be an amine that is converted to a sulfhydryl group by reaction with 2-Iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation. Functional group A or B in any of the above examples could also be a photoreactive group such as aryl azide (including halogenated aryl azide), diazo, benzophenone, alkyne or diazirine derivative.

Reactions of the amine, hydroxyl, sulfhydryl, carboxylate groups yield chemical bonds that are described as amide, amidine, disulfide, ethers, esters, enamine, imine, urea, isothiourea, isourea, sulfonamide, carbamate, alkylamine bond (secondaryamine), carbon-nitrogen single bonds in which the carbon contains a hydroxyl group, thioether, diol, hydrazone, diazo, or sulfone".

If functional group A is an aldehyde or ketone then function B can be (but not restricted to) an hydrazine, hydrazide derivative, amine (to form a Schiff Base that may or may not be reduced by reducing agents such as NaCNBH3) or hydroxyl compound to form a ketal or acetal.

Yet another approach is to have one difunctional monomer so that

A-A plus another agent yields -(A-A)-.

If function A is a sulfhydryl group then it can be converted to disulfide bonds by oxidizing agents such as iodine (I2) or NaIO4 (sodium periodate), or oxygen (O2). Function A can also be an amine that is converted to a sulfhydryl group by reaction with 2-iminothiolate (Traut's reagent) which then undergoes oxidation and disulfide formation. Disulfide derivatives (such as a pyridyl disulfide or 5-thio-2-nitrobenzoic acid{TNB} derivatives) can also be used to catalyze disulfide bond formation.

Functional group A or B in any of the above examples could also be a photoreactive group such as aryl azides, halogenated aryl azides, diazo, benzophenones, alkynes or diazirine derivatives.

Reactions of the amine, hydroxyl, sulfhydryl, carboxylate groups yield chemical bonds that are described as amide, amidine, disulfide, ethers, esters, enamine, urea, isothiourea, isourea, sulfonamide, carbamate, carbon-nitrogen double bond (imine), alkylamine bond (secondary amine), carbon-nitrogen single bonds in which the carbon contains a hydroxyl group, thio-ether, diol, hydrazone, diazo, or sulfone.

Chain Polymerization: In chain-reaction polymerization growth of the polymer occurs by successive addition of monomer units to limited number of growing chains. The initiation and propagation mechanisms are different and there is usually a chain-terminating step. The polymerization rate remains constant until the monomer is depleted.

Monomers containing vinyl, acrylate, methacrylate, acrylamide, methaacrylamide groups can undergo chain reaction which can be radical, anionic, or cationic. Chain polymerization can also be accomplished by cycle or ring opening polymerization. Several different types of free radical initiatiors could be used that include peroxides, hydroxy peroxides, and azo compounds such as 2,2'-Azobis(-amidinopropane) dihydrochloride (AAP). A compound is a material made up of two or more elements.

Types of Monomers: A wide variety of monomers can be used in the polymerization processes. These include positive charged organic monomers such as amines, imidine, guanidine, imine, hydroxylamine, hydrozyine, heterocycles (like imidazole, pyridine, morpholine, pyrimidine, or pyrene. The amines could be pH-sensitive in that the pKa of the amine is within the physiologic range of 4 to 8. Specific amines include spermine, spermidine, N,N'-bis(2-aminoethyl)-1,3-propanediamine (AEPD), and 3,3'-Diamino-N,N-dimethyl-dipropylammonium bromide.

Monomers can also be hydrophobic, hydrophilic or amphipathic. Amphipathic compounds have both hydrophilic (water-soluble) and hydrophobic (water-insoluble) parts. Hydrophilic groups indicate in qualitative terms that the chemical moiety is water-preferring. Typically, such chemical groups are water soluble, and are hydrogen bond donors or acceptors with water. Examples of hydrophilic groups include compounds with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups. Monomers can also be intercalating agents such as acridine, thiazole organge, or ethidium bromide.

Other Components of the Monomers and Polymers: The polymers have other groups that increase their utility. These groups can be incorporated into monomers prior to polymer formation or attached to the polymer after its formation. These groups include: Targeting Groups—such groups are used for targeting the polymer-nucleic acid complexes to specific cells or tissues. Examples of such targeting agents include agents that target to the asialoglycoprotein receptor by using asiologlycoproteins or galactose residues. Other proteins such as insulin, EGF, or transferrin can be used for targeting. Protein refers to a molecule made up of 2 or more amino acid residues connected one to another as in a polypeptide. The amino acids may be naturally occurring or synthetic. Peptides that include the RGD sequence can be used to target many cells. Peptide refers to a linear series of amino acid residues connected to one another by peptide bonds between the alpha-amino group and carboxyl group of contiguous amino acid residues. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

After interaction of the supramolecular complexes with the cell, other targeting groups can be used to increase the delivery of the drug or nucleic acid to certain parts of the cell. For example, agents can be used to disrupt endosomes and a nuclear localizing signal (NLS) can be used to target the nucleus.

A variety of ligands have been used to target drugs and genes to cells and to specific cellular receptors. The ligand may seek a target within the cell membrane, on the cell membrane or near a cell. Binding of ligands to receptors typically initiates endocytosis. Ligands could also be used for DNA delivery that bind to receptors that are not endocytosed. For example peptides containing RGD peptide sequence that bind integrin receptor could be used. In addition viral proteins could be used to bind the complex to cells. Lipids and steroids could be used to directly insert a complex into cellular membranes.

The polymers can also contain cleavable groups within themselves. When attached to the targeting group, cleavage leads to reduce interaction between the complex and the receptor for the targeting group. Cleavable groups include but are not restricted to disulfide bonds, diols, diazo bonds, ester bonds, sulfone bonds, acetals, ketals, enol ethers, enol esters, enamines and imines.

Reporter or marker molecules are compounds that can be easily detected. Typically they are fluorescent compounds such as fluorescein, rhodamine, texas red, CY-5, CY-3 or dansyl compounds. They can be molecules that can be detected by UV or visible spectroscopy or by antibody interactions or by electron spin resonance. Biotin is another reporter molecule that can be detected by labeled avidin. Biotin could also be used to attach targeting groups.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations. A charged polymer is a polymer that contains residues, monomers, groups, or parts with a positive or negative charge and whose net charge can be neutral, positive, or negative.

Signals

In a preferred embodiment, a chemical reaction can be used to attach a signal to a nucleic acid complex. The signal is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The signal can be a protein, peptide, lipid, steroid, sugar, carbohydrate, nucleic acid or synthetic compound. The signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, Golgi apparatus, trans Golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin Al and the ER-retaining signal (KDEL sequence; SEQ ID 1), viral components such as influenza virus hemagglutinin subunit HA-2 peptides and other types of amphipathic peptides.

Cellular receptor signals are any signal that enhances the association of the gene or particle with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Other Definitions:

Extravascular means outside of a vessel such as a blood vessel. Extravascular space means an area outside of a vessel. Space may contain biological matter such as cells and does not imply empty space.

Extravasation means the escape of material such as compounds and complexes from the vessel into which it is introduced into the parenchymal tissue or body cavity.

The process of delivering a polynucleotide to a cell has been commonly termed "transfection" or the process of "transfecting" and also it has been termed "transformation". The polynucleotide could be used to produce a change in a cell that can be therapeutic. The delivery of polynucleotides or genetic material for therapeutic and research purposes is commonly called "gene therapy". The polynucleotides or genetic material being delivered are generally mixed with transfection reagents prior to delivery.

The polyampholyte complex is a complex having the potential to react with biological components. More particularly, polyampholyte complexes utilized in this specification are designed to change the natural processes associated with a living cell. For purposes of this specification, a cellular natural process is a process that is associated with a cell before delivery of a polyampholyte complex. In this specification, the cellular production of, or inhibition of a material, such as a protein, caused by a human assisting a molecule to an in vivo cell is an example of a delivered biologically active compound. Pharmaceuticals, proteins, peptides, polypeptides, hormones, cytokines, antigens, viruses, oligonucleotides, and nucleic acids are examples that can be components of polyampholyte complexes.

The term "nucleic acid" is a term of art that refers to a polymer containing at least two nucleotides. "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nucleic acid includes deoxyribonucleic acid (DNA) and ribonucleic acid (RNA). DNA may be in the form of antisense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. "Anti-sense" is a polynucleotide that interferes with the function of DNA and/or RNA. This may result in suppression of expression. Natural nucleic acids have a phosphate backbone, artificial nucleic acids may contain other types of backbones, nucleotides, or bases. These include PNAs (peptide nucleic acids), phosphothionates, and other variants of the phosphate backbone of native nucleic acids. In addition, DNA and RNA may be single, double, triple, or quadruple stranded. "Expression cassette" refers to a natural or recombinantly produced polynucleotide molecule which is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The term "naked polynucleotides" indicates that the polynucleotides are not associated with a transfection reagent or other delivery vehicle that is required for the polynucleotide to be delivered to the cardiac muscle cell. A "transfection reagent" is a compound or compounds used in the prior art that bind(s) to or complex(es) with oligonucleotides and polynucleotides, and mediates their entry into cells. The transfection reagent also mediates the binding and internalization of oligonucleotides and polynucleotides into cells. Examples of transfection reagents include cationic liposomes and lipids, polyamines, calcium phosphate precipitates, histone proteins, polyethylenimine, and polylysine complexes. It has been shown that cationic proteins like histones and protamines, or synthetic polymers like polylysine, polyarginine, polyornithine, DEAE dextran, polybrene, and polyethylenimine may be effective intracellular delivery agents, while small polycations like spermine may be ineffective. Typically, the transfection reagent has a net positive charge that binds to the oligonucleotide's or polynucleotide's negative charge. The transfection reagent mediates binding of oligonucleotides and polynucleotides to cells via its positive charge (that binds to the cell membrane's negative charge) or via ligands that bind to receptors in the cell. For example, cationic liposomes or polylysine complexes have net positive charges that enable them to bind to DNA or RNA. Polyethylenimine, which facilitates gene expression without additional treatments, probably disrupts endosomal function itself.

Other vehicles are also used, in the prior art, to transfer genes into cells. These include complexing the polynucleotides on particles that are then accelerated into the cell. This is termed "biolistic" or "gun" techniques. Other methods include "electroporation," in which a device is used to give an electric charge to cells. The charge increases the permeability of the cell.

Charge density is the term used to describe the electrical charge per unit area, for example, on a polymer.

Ionic (electrostatic) interactions are the non-covalent association of two or more substances due to attractive forces between positive and negative charges, or partial positive and partial negative charges.

Condensed Nucleic Acids: Condensing a polymer means decreasing the volume that the polymer occupies. An example of condensing nucleic acid is the condensation of DNA that occurs in cells. The DNA from a human cell is approximately one meter in length but is condensed to fit in a cell nucleus that has a diameter of approximately 10 microns. The cells condense (or compacts) DNA by a series of packaging mechanisms involving the histones and other chromosomal proteins to form nucleosomes and chromatin. The DNA within these structures is rendered partially resistant to nuclease DNase) action. The process of condensing polymers can be used for delivering them into cells of an organism.

A delivered polymer can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Condensed nucleic acids may be delivered intravasculary, intrarterially, intravenously, orally, intraduodenaly, via the jejunum (or ileum or colon), rectally, transdermally, subcutaneously, intramuscularly, intraperitoneally, intraparenterally, via direct injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands. "Delivered" means that the polynucleotide becomes associated with the cell. The polynucleotide can be on the membrane of the cell or inside the cytoplasm, nucleus, or other organelle of the cell.

An intravascular route of administration enables a polymer or polynucleotide to be delivered to cells more evenly distributed and more efficiently expressed than direct injections. Intravascular herein means within a tubular structure called a vessel that is connected to a tissue or organ within the body. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

An administration route involving the mucosal membranes is meant to include nasal, bronchial, inhalation into the lungs, or via the eyes.

Recharging Condensed Nucleic Acids

Polyions for gene therapy and gene therapy research can involve anionic systems as well as charge neutral or charge-positive systems. The ionic polymer can be utilized in "recharging" (another layer having a different charge) the condensed polynucleotide complex. The resulting recharged complex can be formed with an appropriate amount of charge such that the resulting complex has a net negative, positive or neutral charge. The interaction between the polycation and the polyanion can be ionic, can involve the ionic interaction of the two polymer layers with shared cations, or can be crosslinked between cationic and anionic sites with a crosslinking system (including cleavable crosslinking systems, such as those containing disulfide bonds). The interaction between the charges located on the two polymer layers can be influenced with the use of added ions to the system. With the appropriate choice of ion, the layers can be made to disassociate from one another as the ion diffuses from the complex into the cell in which the concentration of the ion is low (use of an ion gradient).

Electrostatic complexes between water-soluble polyelectrolytes have been studied widely in recently ears. Complexes containing DNA as a polyanionic constituent only recently came to the attention because of their potential use in gene therapy applications such as non-viral gene transfer preparations (polyplexes) for particle delivery to a cell. Strong polyelectrolytes, polyanion/polycation complexes, are usually formed at a 1:1 charge stoichiometrically. A charge ratio 1:1 complex between DNA and Poly-L-Lysine (PLL) also has been demonstrated in the prior art.

Polyanions effectively enhance the gene delivery/gene expression capabilities of all major classes of polycation gene delivery reagents. In that regard, we disclose the formation of negatively charged tertiary complexes containing nucleic acid, PLL, and succinic anhydride-PLL (SPLL) complexes. SPLL is added to a cationic nucleic acid/PLL complex in solution. Nucleic acid at the core of such complexes remains condensed, in the form of particles ~50 nm in diameter. DNA and PLL binds SPLL in 1:1:1 complex with SPLL providing a net negative charge to the entire complex. Such small negatively charged particles are useful for non-viral gene transfer applications.

One of the advantages that flow from recharging DNA particles is reducing their non-specific interactions with cells and serum proteins ((Wolfert et al. Hum. Gene Therapy 7:2123-2133 (1996); Dash et al., Gene Therapy 6:643-650 (1999); Plank et al., Hum. Gene Ther. 7:1437-1446 (1996); Ogris et al., Gene Therapy 6:595-605 (1999); Schacht et al. Brit. Patent Application 9623051.1 (1996))

A wide a variety of polyanions can be used to recharge the DNA/polycation particles. They include (but not restricted to): Any water-soluble polyanion can be used for recharging purposes including succinylated PLL, succinylated PEI (branched), polyglutamic acid, polyaspartic acid, polyacrylic acid, polymethacrylic acid, polyethylacrylic acid, polypropylacrylic acid, polybutylacrylic acid, polymaleic acid, dextran sulfate, heparin, hyaluronic acid, polysulfates, polysulfonates, polyvinyl phosphoric acid, polyvinyl phosphonic acid, copolymers of polymaleic acid, polyhydroxybutyric acid, acidic polycarbohydrates, DNA, RNA, negatively charged proteins, pegylated derivatives of above polyanions, pegylated derivatives carrying specific ligands, block and graft copolymers of polyanions and any hydrophilic polymers (PEG, poly(vinylpyrrolidone), poly(acrylamide), etc).

DNA condensation assays based on the effect of concentration-dependent self-quenching of covalently-bound fluorophores upon DNA collapse indicated essentially the same phenomenon described in the prior art. Polyanions with high charge density (polymethacrylic acid, pMAA and polyaspartic acid, pAsp) were able to decondense DNA prior to those that complexed with PLL while polyanions with lower charge density (polyglutamic acid, pGlu, SPLL) failed to decondense DNA. Together with z-potential measurements, these data represent support for the presence of negatively charged condensed DNA particles. These particles are approximately 50 nm in diameter in low salt buffer as measured by atomic force microscopy which revealed particles of spheroid morphology. This places them very close in size to binary DNA/PLL particles. Particles prepared using various pC/pA polyampholytes can be used to form similar condensed DNA particles.

In another preferred embodiment, the polyanion can be covalently attached to the polycation using a variety of chemical reactions without the use of crosslinker. The polyanion can contain reactive groups that covalently attach to groups on the polycation. This results in the formation of a polyampholyte The types of reactions are similar to those discussed above in the section on step polymerization.

In another preferred embodiment the attachment of the recharged complex can be enhanced by using chelators and crown ethers, preferably polymeric.

In one preferred embodiment the DNA/polycation complexes are initially formed by adding only a small excess of polycation to nucleic acid (in charge ratio which is defined as ratio of polycation total charge to polyanion total charge at given pH). The charge ratio of polycation to nucleic acid charge could be less than 2, less than 1.7, less than 1.5 or even less than 1.3. This would be preferably done in low ionic strength solution so as to avoid the complexes from flocculation. Low ionic strength solution means solution with total monovalent salt concentration less than 50 mM. Then the polyanion is added to the mixture and only a small amount of "blank" particles are formed. "Blank" particles are particles that contain only polycation and polyanion and no nucleic acid.

In another preferred embodiment, the polycation is added to the nucleic acid in charge excess but the excess polycation that is not in complex with the nuclei acid is removed by purification. Purification means removing of charged polymer using centrifugation, dialysis, chromatography, electrophoresis, precipitation, extraction.

Yet in another preferred embodiment a ultracentrifugation procedure (termed "centrifugation step") is used to reduce the amount of excess polycation, polyanion, or "blank" particles. The method is based on the phenomenon that only dense DNA-containing particles can be centrifuged through 10% sucrose solution at 25,000 g. After centrifugation purified complex is at the bottom of the tube while excess of polyanion and "blank" particles stay on top. In modification of this experiment 40% solution of metrizamide can be used as a cushion to collect purified DNA/polycation/polyanion complex on the boundary for easy retrieval.

The attachment of the polyanion to the DNA/polycation complex enhance stability but can also enable a ligand or signal to be attached to the DNA particle. This is accomplished by attaching the ligand or signal to the polyanion which in turn is attached to the DNA particle. A dialysis step or centifugation step can be used to reduce the amount of free polyanion containing a ligand or signal that is in solution and not complexed with the DNA particle. One approach is to replace the free, uncomplexed polyanion containing a ligand or signal with free polyanion that does not contain a ligand or signal.

Yet in another preferred embodiment a polyanion used for charge reversal is modified with neutral hydrophilic polymer for steric stabilization of the whole complex. The complex formation of DNA with pegylated polycations results in substantial stabilization of the complexes towards salt- and serum-induced flocculation (Wolfert et al. Hum. Gene Therapy 7:2123-2133 (1996), Ogris et al., Gene Therapy 6:595-605 (1999). We have demonstrated that modification of polyanion in triple complex also significantly enhances salt and serum stability.

In another preferred embodiment a polyanion used for charge reversal is cleavable. One can imagine two ways to design a cleavable polyion: 1. A polyion cleavable in backbone, 2. A polyion cleavable in side chain. First scenario would comprise monomers linked by labile bonds such as disulfide, diols, diazo, ester, sulfone, acetal, ketal, enol ether, enol ester, imine and enamine bonds. Second scenario would involve reactive groups (i.e. electrophiles and nucleophiles) in close proximity so that reaction between them is rapid. Examples include having corboxylic acid derivatives (acids, esters and amides) and alcohols, thiols, carboxylic acids or amines in the same molecule reacting together to make esters, thiol esters, anhydrides or amides. In one specific preferred embodiment the polyion contains an ester acid such as citraconnic acid, or dimethylmaleyl acid that is connected to a carboxylic, alcohol, or amine group on the polyion.

Cleavable means that a chemical bond between atoms is broken. Labile also means that a chemical bond between atoms is breakable. Crosslinking refers to the chemical attachment of two or more molecules with a bifunctional reagent. A bifunctional reagent is a molecule with two reactive ends. The reactive ends can be identical as in a homobifunctional molecule, or different as in a heterobifunctional molecule.

EXAMPLES

Example 1

Synthesis of lPEI-pMAA and lPEI-pGlu complexes.

The following polyions were used for the reaction: lPEI (Mw=25 kDa, Polysciences), pMAA (Mw=9.5 kDa, Aldrich), pGlu (Mw=49 kDa, Sigma). For analytical purposes pAs covalently labeled with rhodamine-ethylenediamine (Molecular Probes) were used for these reactions (degree of carboxy group modification<2%). Absorbance of the pAs was used to trace pAs and conjugates during size exclusion chromatography. PMAA (or pGlu, 1 mg in 100 μL water) was activated in the presence of water-soluble carbidiimide (EDC, 100 μg) and N-hydroxysulfosuccinimide (100 μg) for 10 min at pH 5.5. Activated pMAA was added to the solution of lPEI (2 mg in 200 μL of 25 mM HEPES, pH 8.0) and incubated for 1 hr at room temperature.

Example 2

Separation of lPEI-pMAA and lPEI-pGlu reaction mixtures using Sepharose 4B-CL column in 1.5 M NaCl.

Figure 2:
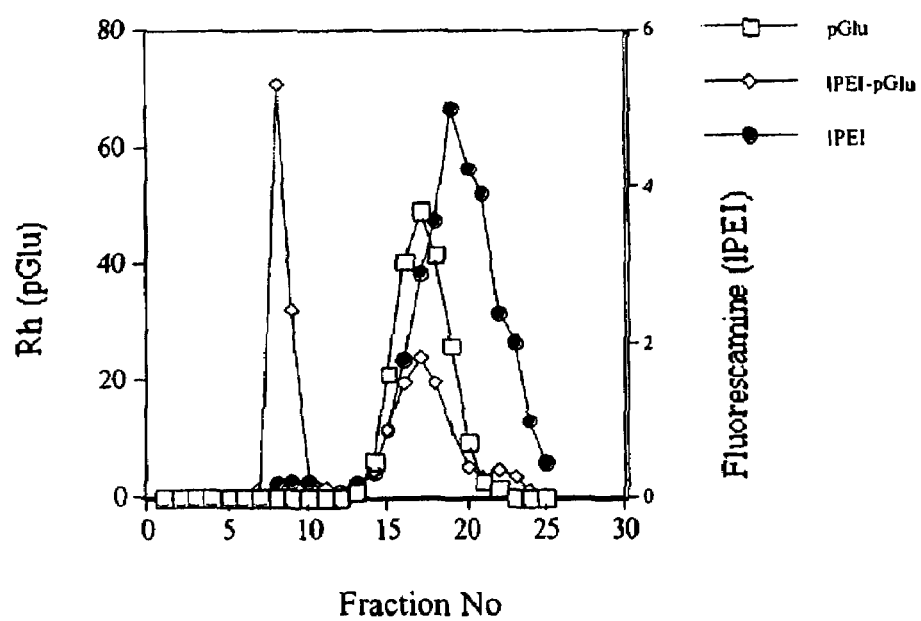
FIG. 2 Isolation of lPEI-pGlu polyampholyte using Example 1 reaction mixture.

After the reaction completion equal volume of 3 M NaCl solution was added to the part of the reaction mixture. This part (0.5 ml) was passes through the Sepharose 4B-CL column (1×25 cm) equlibrated in 1.5 M NaCl. Volume of the fractions collected was 1 ml. Rhodamine fluorescence was measured in each fraction. Linear PEI was measured using fluorescamine reaction. The amount of polyampholyte in the lPEI-pGlu reaction mixture is about 50% (see FIG. 2).

Example 3

HUH7 mouse liver cell transfection using DNA/lPEI-pA polyampholyte mixtures.

Figure 3:
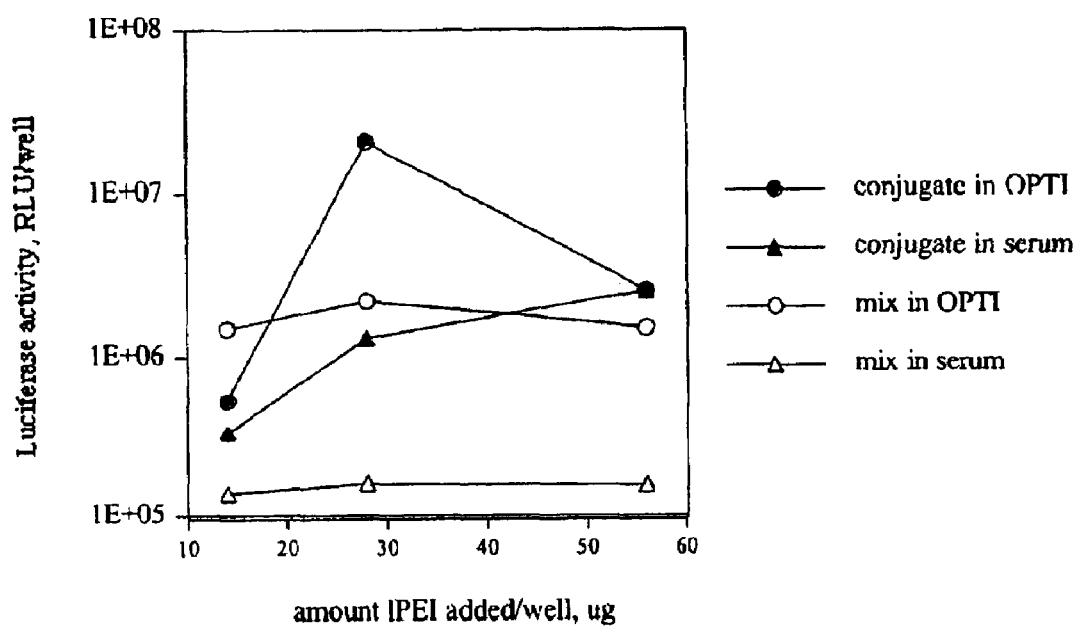
FIG. 3 Transfection of HUH7 cells using lPEI-pGlu polyampholyte using Example 1 reaction mixture.
Figure 4:
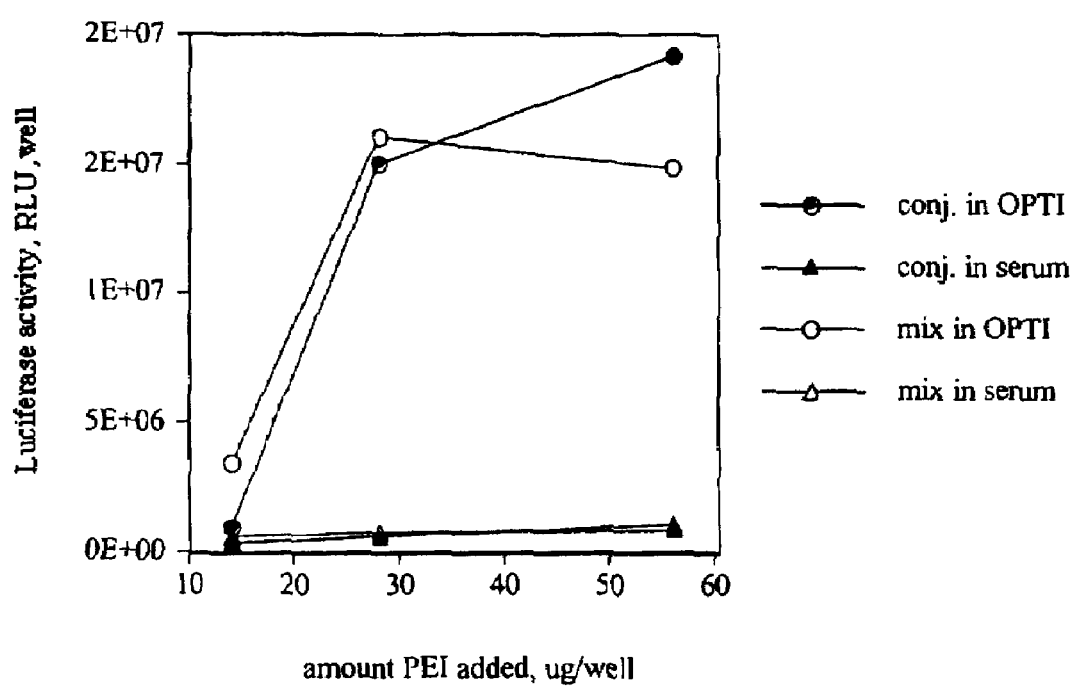
FIG. 4 Transfection of HUH7 cells using lPEI-pMAA polyampholyte using Example 1 reaction mixture.

Part of the polyampholyte reaction mixtures lPEI-pMAA and lPEI-pGlu were used to transfect HUH7 cells in culture. Non-covalent mixtures of lPEI with pMAA and pGlu mixed in the same ratios as for conjugates were used as the controls. Luciferase-encoded plasmid pCIluc (2 μg per 35 mm well) was used for transfection in OPTIMEM (cell medium) and OPTIMEM supplemented with 10% bovine serum. Amount of polyampholyte added is indicated on the basis of lPEI content. Results of this experiment are shown on FIGS. 3 and 4. There is a strong enhancement of transfection for polyampholytes in case of weaker pA conjugate (lPEI-pGlu, FIG. 3) and almost no difference in transfection abilities of conjugates and mixtures for stronger pA (lPEI-pMAA, FIG. 4) in accordance to FIG. 1 scheme.

Example 4

Optimized Synthesis of lPEI-pGlu Polyampholyte

Figure 5:
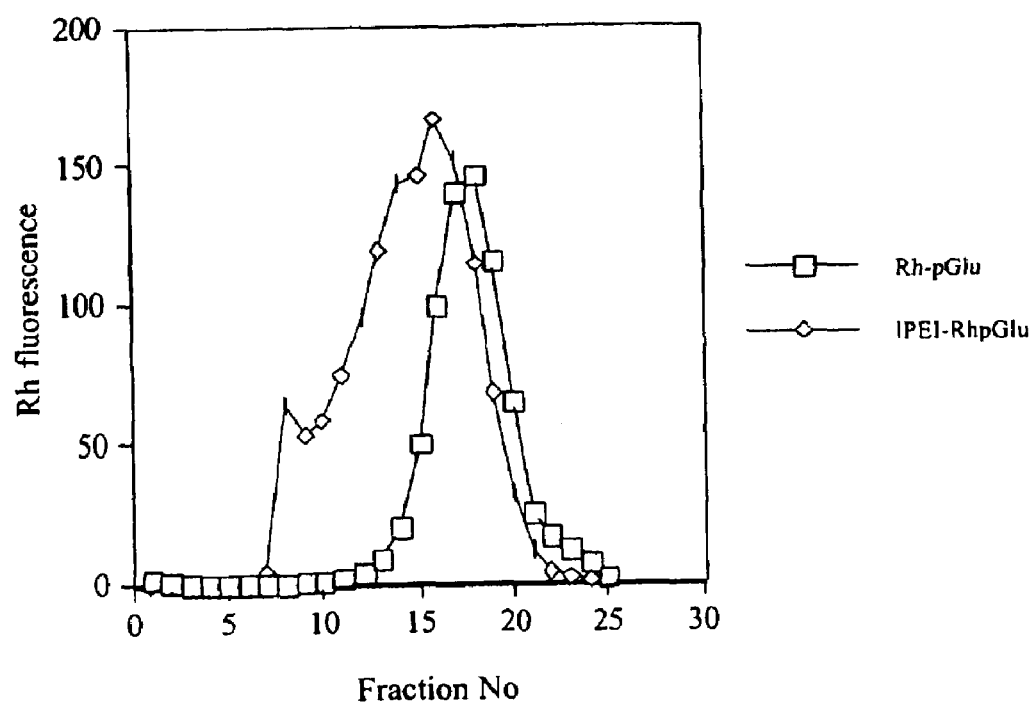
FIG. 5 Sepharose 4B-CL chromatography of rhodamine-labeled pGlu and lPEI-pGlu polyampholyte.

Rhodamine-labeled polyglutamic acid (pGlu, 150 uL, 20 mg/ml, titrated to pH 5.0) was activated with water-soluble [3'-(dimethylaminopropyl)-3-ethyl]carbodiimide (EDC, 15 ul, 100 mg/ml in DMSO) and sulfosuccinimide (SNHS, 15 um, 100 mg/ml in water) for 10 min. Then linear PEI (lPEI, 150 ul, 20 mg/ml) was added to the mixture, pH was adjusted to 8.0 and the mixture was allowed to stand for 2 hrs at room temperature. After this the mixture was passed through Sepharose 4B-CL column (1×20 cm) equilibrated with 1.5 M NaCl solution (FIG. 5). Rhodamine fluorescence was measured in each fraction. Fractions 10-14 were pooled, dialysed against water and freeze-dried to yield purified polyampholyte.

Example 5

HUH7 mouse liver cell transfection using DNA/lPEI-pA polyampholyte mixtures in the presence of 100% serum.

Figure 6:
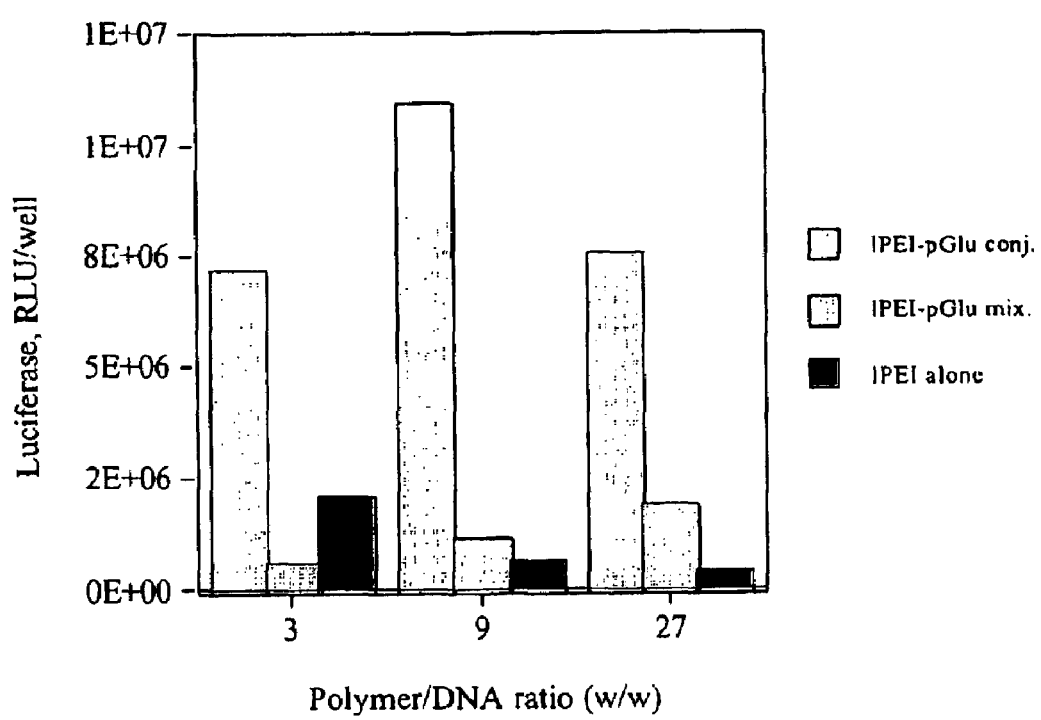
FIG. 6 Luciferase expression in HUH7 cells in vitro in 100% bovine serum aided by covalent lPEI-pGlu polyampholyte as compared to lPEI-pGlu non-covalent mixture and lPEI alone.

The luciferase encoding plasmid pCILuc was used for in vitro and in vivo gene transfer experiments. The DNA/polymer complexes were formed in 5 mM HEPES, 50 mM NaCl, 0.29 M glucose, pH 7.5 at DNA concentration of 50 ug/ml. HUH7 mouse liver cells were subconfluently seeded in 12-well plates. The complexes (1 ug of DNA) were added directly to 1 ml of 100% bovine serum into each well and incubated with cells for 4 hrs. After this step the cells were washed with OPTI-MEM media, supplemented with fresh media and maintained for additional 48 hrs. After this period of time the cells were harvested, lysed and processed for luciferase expression measurements. Non-covalent mixture of lPEI and pGlu as well as lPEI alone were used a controls in this experiment (FIG. 6). As one can see, the covalent conjugate of lPEI and pGlu gave significantly higher gene transfer activity in high range of polymer/DNA ratios as compared to controls.

Example 6

Synthesis of Branched PEI (brPEI)—pGlu and brPEI-pAsp Polyampholytes

Polyglutamic acid (pGlu, 2.28 mg in 172 ul of water, pH 5.5) or polyaspartic acid (pAsp, 2 mg in 172 ul of water) were activated in the presence of 100 ug of EDC and SNHS each for 10 min at room temperature. BrPEI (4 mg) and 2.5 M NaCl (0.5 ml) solutions were added to the activated polyanion. The reaction mixture was allowed to incubate for 5 hrs at room temperature. Resulting brPEI-based polyampholytes were dialyzed against water and freeze-dried.

Example 7

In vivo gene transfer activity of DNA/polyampholyte complexes prepared from branched PEI.

BrPEI-pGlu and brPEI-pAsp polyampholytes were mixed with DNA at different w/w ratios in 5 mM HEPES, 0.29 M glucose, pH 7.5 at the DNA concentration of 0.2 mg/ml. The complexes (0.25 ml per animal) were intravenously injected into mouse tail vein (2 animals per group). The animals were sacrificed 24 hrs after injection and the lungs were processed for luciferase activity. The results of in vivo gene transfer are presented in Table 1:

TABLE 1

| Ratio (w/w) | DNA/brPEI | DNA/brPEI-pAsp | DNA/brPEI-pGlu |
|---|---|---|---|
| 1:1 | 600, non-toxic | 88,000, non-toxic | 34,000, non-toxic |
| 1:2 | All died | 600,000, one died | 3,900,000, non-toxic |
| 1:3 | n/a | n/a | 4,800,000, one died |

Luciferase activity (RLU) in lungs after intravenous administration of DNA/brPEI-based polyampholytes in mice. Each animal received 50 ug of DNA in 0.25 ml of isotonic glucose solution. There were 2 animals per group. Survival of all animals in the group marked as non-toxic.

As one can see, complexing DNA with brPEI-based polyampholytes results in effective preparations for DNA delivery to parenchymal cells. BrPEI alone is ineffective at low weight ratios and toxic at higher ratios. Covalent conjugation of polyanions results in significant increase in gene transfer efficacy in lungs accompanying with reduction of toxicity.

The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for enhancing delivery of a polyion to a cell, comprising:
 a) forming a complex of polyampholyte having groups with pKa's within the physiological range of 4 to 8 and polyion; and,
 b) delivering the complex into a cell.

2. The process of claim 1 wherein the polyampholyte contains maleamic acid.

3. The process of claim 2 wherein the polyampholyte is delivered to a cell in vivo.

4. A deliverable complex, comprising: a polyion, and a polyampholyte having groups with pKa's within the physiological range of 4 to 8 wherein the complex is structured to enter a mammalian cell.

5. The complex of claim 4 wherein the polyampholyte contains a bond that is cleavable by a decrease in pH.

6. The complex of claim 5 wherein the polyampholyte contains maleamic acid.

7. The complex of claim 6 wherein the polyampholyte is membrane-disruptive upon cleavage.

8. The complex of claim 7 wherein the polyion comprises a polynucleotide.

9. The complex of claim 8 wherein the polynucleotide comprises an double strand RNA oligonucleotide.

10. The complex of claim 1 wherein the polyampholyte is amphipathic.

11. The complex of claim 1 wherein the polyampholyte contains targeting groups.

12. The complex of claim 11 wherein the targeting group comprises a ligand for a cellular receptor.

13. The complex of claim 12 wherein the cellular receptor consists of an asialoglycoprotein receptor.

14. The complex of claim 1 wherein the polyampholyte contains one or more polyethylene glycol groups.

* * * * *